United States Patent
Haufe et al.

(10) Patent No.: US 10,703,847 B2
(45) Date of Patent: Jul. 7, 2020

(54) VINYL-TERMINATED PREPOLYMERS HAVING LOW VISCOSITY AND GOOD WATER SOLUBILITY

(71) Applicant: SIKA TECHNOLOGY AG, Baar (CH)

(72) Inventors: Markus Haufe, Zürich (CH); Max Hug, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 137 days.

(21) Appl. No.: 15/579,081

(22) PCT Filed: Jun. 1, 2016

(86) PCT No.: PCT/EP2016/062374
§ 371 (c)(1),
(2) Date: Dec. 1, 2017

(87) PCT Pub. No.: WO2016/193302
PCT Pub. Date: Dec. 8, 2016

(65) Prior Publication Data
US 2018/0171054 A1  Jun. 21, 2018

(30) Foreign Application Priority Data

Jun. 3, 2015  (EP) .................................. 15170539

(51) Int. Cl.
| | |
|---|---|
| C08G 18/10 | (2006.01) |
| C04B 26/00 | (2006.01) |
| C08G 18/76 | (2006.01) |
| C08F 290/06 | (2006.01) |
| C08G 18/67 | (2006.01) |
| C08G 18/79 | (2006.01) |
| C08G 18/28 | (2006.01) |
| C04B 26/16 | (2006.01) |
| C04B 24/28 | (2006.01) |
| C08G 18/48 | (2006.01) |
| C04B 24/26 | (2006.01) |
| C08G 18/12 | (2006.01) |
| C08G 18/72 | (2006.01) |
| C08G 18/75 | (2006.01) |
| C08G 18/78 | (2006.01) |
| A61F 13/00 | (2006.01) |
| C04B 103/32 | (2006.01) |
| C04B 103/00 | (2006.01) |
| C04B 111/00 | (2006.01) |
| C04B 103/30 | (2006.01) |

(52) U.S. Cl.
CPC ...... *C08F 290/067* (2013.01); *C04B 24/2658* (2013.01); *C04B 24/282* (2013.01); *C04B 26/16* (2013.01); *C08G 18/12* (2013.01); *C08G 18/283* (2013.01); *C08G 18/485* (2013.01); *C08G 18/4833* (2013.01); *C08G 18/4837* (2013.01); *C08G 18/672* (2013.01); *C08G 18/675* (2013.01); *C08G 18/725* (2013.01); *C08G 18/755* (2013.01); *C08G 18/7621* (2013.01); *C08G 18/7893* (2013.01); *C08G 18/792* (2013.01); *A61F 2013/00748* (2013.01); *C04B 2103/0051* (2013.01); *C04B 2103/0059* (2013.01); *C04B 2103/30* (2013.01); *C04B 2103/32* (2013.01); *C04B 2111/00724* (2013.01)

(58) Field of Classification Search
CPC .. C08G 18/12; C08G 18/283; C08G 18/4833; C08G 18/4837; C08G 18/485; C08G 18/672; C08G 18/675; C08G 18/725; C08G 18/755; C08G 18/7621; C08G 18/7893; C08G 18/792; C08F 290/067; C08B 24/2658; C08B 24/282; C08B 26/16; C04B 24/2658; C04B 24/282; C04B 26/16

See application file for complete search history.

(56) References Cited

U.S. PATENT DOCUMENTS

| | | | | |
|---|---|---|---|---|
| 4,312,972 A | * | 1/1982 | Khanna ............... | C08F 290/067 521/159 |
| 4,749,592 A | * | 6/1988 | Gasper ................ | C08F 299/022 427/140 |
| 2008/0300338 A1 | | 12/2008 | Wagner et al. | |

(Continued)

FOREIGN PATENT DOCUMENTS

| | | |
|---|---|---|
| EP | 2 164 881 B1 | 8/2011 |
| EP | 2 581 396 A1 | 4/2013 |

(Continued)

OTHER PUBLICATIONS

JP-2003201331_Jul. 2003_English Translation.*

(Continued)

*Primary Examiner* — Michael L Leonard

(74) *Attorney, Agent, or Firm* — Oliff PLC

(57) ABSTRACT

A polyether having a functional group that is reactive to isocyanate with at least one polyisocyanate, which has an average isocyanate functionality in the range of 2.4 to 3.5, and at least one vinyl compound, which has a functional group that is reactive to isocyanate, wherein the molar ratio of polyether to vinyl compound lies in the range of 3:1 to 1:3 and the ratio of the sum of the molar quantities of polyether and vinyl compounds to isocyanate groups lies in the range of 1.5:1 to U.5. Corresponding vinylterminated prepolymers have the advantage of low visocity together with good water solubility and therefore can be used advantageously for applications as injection agents.

20 Claims, No Drawings

(56) References Cited

U.S. PATENT DOCUMENTS

2013/0095331 A1* 4/2013 Ludewig ............ C08G 18/4833
428/425.1
2015/0247076 A1* 9/2015 Kou ................... C08G 18/6225
156/327

FOREIGN PATENT DOCUMENTS

| JP | 2003-201331 A | | 7/2003 |
|---|---|---|---|
| JP | 2003201331 A | * | 7/2003 |
| WO | 2007/063027 A1 | | 6/2007 |

OTHER PUBLICATIONS

Dec. 5, 2017 International Preliminary Report on Patentability issued in International Patent Application No. PCT/EP2016/062374.

Aug. 3, 2016 International Search Report issued in International Patent Application No. PCT/EP2016/062374.

Mar. 3, 2020 Office Action issued in Brazilian Patent Application No. BR112017025558-8.

* cited by examiner

VINYL-TERMINATED PREPOLYMERS HAVING LOW VISCOSITY AND GOOD WATER SOLUBILITY

TECHNICAL FIELD

The invention relates to vinyl-terminated prepolymers based on polyethers, which are prepared by the reaction of polyethers having isocyanate-reactive functional groups with isocyanates of mean isocyanate functionality in the range from 2.4 to 3.5, and vinyl compounds likewise having an isocyanate-reactive functional group, wherein the polyethers relative to the vinyl compounds and the sum total of the molar amounts of the polyethers and vinyl compounds relative to isocyanate groups are present in particular ratios. The present invention further relates to processes for producing corresponding vinyl-terminated prepolymers, and to the use thereof as injection media or a constituent of injection media, or for production of superabsorbents and concrete plasticizers.

STATE OF THE ART

Conventional free-radical-curing systems are generally formed from monomers such as allyl, vinyl, methacryloyl and acryloyl compounds. In the production of hydrophilic systems, monomers having hydrophilic groups, for example in the form of hydroxyl or ammonium groups, are used. If hydrophilic polymers are prepared directly by free-radical polymerization, i.e. not via the indirect route of polymerization of nonpolar ester monomers and subsequent hydrolysis thereof to alcohols, monomers such as hydroxyalkyl (meth)acrylates, (meth)acrylic acid or polyalkylene glycols wherein the terminal hydroxyl functions have been modified with (meth)acrylates are frequently used. One particular example of such polyalkylene glycol (meth)acrylates is that of polyethylene glycol dimethacrylates which, after polymerization, have favorable properties as sealants with respect to water. One example of the use of polyalkylene glycol di(meth)acrylates is to be found in EP 2 164 881 B1, in which sealants based on polyethylene glycol dimethacrylates having a weight-average molecular weight of more than 5000 g/mol are proposed. Compared to corresponding sealants based on polyethylene glycols having relatively low molecular weight, the sealants claimed are said to feature improved swellability and elevated ultimate elongation.

In injection applications, very low viscosities are indispensable since the monomers have to be brought through tight passages to the desired site of application, and should also very substantially completely fill a cavity to be filled. This is especially true of crack sealing applications, in which the material introduced has to be distributed within very narrow gaps. While monomers such as hydroxyalkyl (meth)acrylates or (meth)acrylic acid have correspondingly low viscosities, the viscosity of polyethylene glycol di(meth)acrylate compounds having molecular masses of >500 Mn increases significantly, which impairs the suitability thereof for injection applications. In spite of this disadvantage, polyethylene glycol di(meth)acrylate compounds are also used in injection applications since these monomers can be converted to swellable polymers.

In the prior art, polyethylene di(meth)acrylate compounds are generally prepared by transesterification of readily available (meth)acrylate esters or by direct esterification of polyethylene glycols. However, preparation via a transesterification in which an alcohol group is eliminated is associated with the drawback that such a reaction product has to be registered under REACh, and this is associated with a loss of time and additional costs. In order to avoid a REACh registration, the by-product can be removed (the transesterification of methyl methacrylate with polyethylene glycol, for example, gives rise to methanol as a by-product which can be removed under reduced pressure), but this too is associated with an additional processing step and hence with higher costs.

Direct esterification of a polyethylene glycol with a vinyl anhydride results in formation of by-products since an acid anion is released as leaving group, for example, in the case of use of an acid anhydride. By-products of this kind on the one hand are subject to obligatory registration under REACh, but on the other hand they also have to be separated from the product obtained and correspondingly processed or disposed of. Separation can be avoided in the case of use of a cyclic anhydride (e.g. maleic anhydride). After the reaction, however, an acid function remains in the product, and so the resulting prepolymers are relatively polar. This in turn can be undesirable in the polymers prepared from the prepolymers.

As well as esterification or transesterification, it is also possible to prepare hydrophilic prepolymers having terminal vinyl functions via NCO/OH or NCO/NH reactions. For example, a conceivable reaction is that of polyether polyols or polyethers having terminal amino functions with an excess of diisocyanate, and the subsequent reaction of the isocyanate-modified polyethers with an unsaturated alcohol or amine compound. In the case of preparation of vinyl-terminated prepolymers via an NCO/OH reaction, however, the relatively high reactivity of the terminal OH groups in the polyethylene glycol has been found to be problematic, and the effect of this is that controlled and stoichiometric reactions are possible only with great difficulty, if at all. As a result, there is always a certain degree of chain extension, which has an adverse effect on the viscosity of the prepolymers prepared.

An approach described in the prior art for reducing the viscosity of polyethylene glycol diacrylates involves using block copolymers based on polyethylene glycol and polypropylene glycol in place of the pure polyethylene glycol diols. The polypropylene glycol component results in a reduction in the viscosity, the extent of which increases with the polypropylene glycol content in the copolymer. However, a disadvantage of this approach is that the water solubility of the resulting prepolymers is adversely affected as the proportion of polypropylene glycol increases. A further problem is that prepolymers of this kind act as surfactants, which can result in unwanted foaming in the ultimate application. Furthermore, the polyethylene glycol/polypropylene glycol block copolymers mentioned are also often so reactive that the reaction with isocyanates forms prepolymers of relatively high viscosity. A further disadvantage is that the polypropylene content has an adverse effect on the swellability of the fully polymerized prepolymers.

EP 2 581 396 describes a process for preparing water-thinnable urethane (meth)acrylates of low viscosity, obtainable by reaction of oligomeric polyisocyanates, polyoxyalkylenemonools, hydroxyalkyl (meth)acrylates and polyoxyalkylenepolyols based on starter molecules having at least three hydroxyl functionalities which have been partly converted by crosslinking with (meth)acrylic acid so as to leave an average of 0.2 to 1.5 hydroxyl functionalities. The water-thinnable urethane (meth)acrylates described are especially intended to be usable as coating compositions, since the viscosity thereof can be adjusted in a variable manner by addition of water.

JP 2003-201331 A describes radiation-curable coating compositions including polyisocyanate derivatives formed from polyisocyanate compounds, specific polyoxyalkylene glycol derivatives and (meth)acrylates containing hydroxyl groups. Via the isocyanate reaction, the polyoxyalkylene glycol derivatives and (meth)acrylates containing hydroxyl groups are covalently bonded to the polyisocyanates.

WO 2007/063027 describes radiation-curable water-emulsifiable polyisocyanates based on reaction products of organic di- or polyisocyanates, compounds having one isocyanate-reactive and one free-radically polymerizable functional group, and a compound having one isocyanate-reactive group and one saturated dispersion-active group. With such polyisocyanates, it is said to be possible to produce surface coatings having improved hardness, scratch resistance, chemical resistance, adhesion and elasticity.

Against this background, there is a need for vinyl-terminated prepolymers based on polyethers, which feature both minimum viscosity and good water solubility. The present invention is concerned with this problem.

SUMMARY OF THE INVENTION

It is accordingly an object of the present invention to improve the vinyl-terminated prepolymers known from the prior art outlined above, and especially to propose prepolymers which feature low viscosity and good water solubility compared to the known systems. The prepolymers should additionally be stable over a prolonged period in aqueous solution, without solidification or polymerization of the materials. Finally, the prepolymers should be preparable via simple reactions that give rise to a minimum level of by-products that have to be removed or disposed of. In spite of these stipulations, the prepolymers should be readily modifiable, in order thus to enable simple matching of the properties to the end use. In a corresponding manner to the known vinyl-terminated prepolymers, the further-developed prepolymers should be free-radically polymerizable.

According to the invention, this is achieved by a vinyl-terminated prepolymer according to claim 1. The present invention is additionally concerned with processes for preparing such vinyl-terminated prepolymers, and with the use thereof as injection media or a constituent of injection media for sealing of built structures, tunnels or mines, for example, the use thereof for production of superabsorbents and the use thereof for production of concrete plasticizers. The present invention additionally also relates to injection media, superabsorbents and concrete plasticizers obtainable by polymerization of the above-specified vinyl-terminated prepolymer, optionally with addition of further vinyl monomers.

In a first aspect, the present invention relates to a vinyl-terminated prepolymer based on polyethers, obtainable by reaction of
i) a polyether having a functional group reactive toward isocyanates with
ii) at least one polyisocyanate having a mean isocyanate functionality in the range from 2.4 to 3.5, and
iii) at least one vinyl compound having a functional group reactive toward isocyanates, wherein the molar ratio of polyether i) to vinyl compound iii) is in the range from 3:1 to 1:3 and the ratio of the sum total of the molar amounts of polyether and vinyl compound to isocyanate groups ii) is in the range from 1.5:1 to 1:1.5.

In the case of the "at least one polyisocyanate" having a mean isocyanate functionality in the range from 2.4 to 3.5, the mean isocyanate functionality refers to the mean molar isocyanate functionality of the constituents of the at least one isocyanate. If the at least one isocyanate consists, for example, of a 1:1 mixture of a diisocyanate and a triisocyanate, this results in a mean isocyanate functionality of 0.5×2+0.5×3=2.5. If the at least one isocyanate consists exclusively of triisocyanates, this results in a mean isocyanate functionality of 1×3=3.0. If the at least one polyisocyanate is a polyisocyanate, the mean molar isocyanate functionality is an integer, i.e. in the present case 3.0.

The "isocyanate-reactive functional groups" are preferably hydroxyl, amino or thiol groups, of which amino and hydroxyl groups are particularly preferred and hydroxyl groups are the most preferred.

"A" functional group reactive toward isocyanates means that said polyethers or the at least one vinyl compound should have exactly one functional group reactive toward isocyanates. If the at least one vinyl compound comprises more than one vinyl compound, the attribute "having a functional group reactive toward isocyanates" should be understood to mean that each of the vinyl compounds has a functional group reactive toward isocyanates.

The expression "(meth)acrylate" hereinafter always covers both methacrylates and acrylates.

In the context of the present invention, unless stated otherwise, the molecular weight refers to the weight-average molecular weight Mw, which can appropriately be determined by GPC with the aid of suitable standards (e.g. polystyrene).

The polyether that forms the basis of the polyether having a functional group reactive toward isocyanates is preferably an appropriately linear polyalkylene glycol in which, with the exception of one OH group, all other functional groups reactive toward isocyanates that were formerly present in the polyalkylene glycol have been provided with a capping group and hence deactivated. For example, an OH group may have been modified to form a ether which is unreactive toward isocyanates. Analogously, an amino group may have been modified to give an amide. However, the only crucial factor in respect of the capping group is that it does not have any functional groups reactive toward isocyanates or any vinyl groups.

The polyether is preferably a polyethylene glycol, polypropylene glycol or a polyethylene glycol/polypropylene glycol copolymer or block copolymer. In respect of polyethylene glycol/polypropylene glycol copolymers, it is additionally considered to be preferable when they have a polypropylene glycol content of 60 mol % or less and preferably 50 mol % or less.

The polyether is more preferably a polyethylene glycol. It is further preferable when the polyether is liquid at room temperature.

The capping group is independently preferably an alkoxy group and more preferably a methoxy group.

With regard to the molecular weight Mw, the polyether having a functional group reactive toward isocyanates is not subject to any significant restrictions, provided that the polyether assures adequate water solubility of the resulting prepolymer. However, it is considered to be appropriate when the molecular weight Mw of the polyether is within the range from 200 to 5000 g/mol, preferably 300 to 2000 g/mol and more preferably 350 to 1800.

Molecular weights of more than 5000, as already indicated above, lead to vinyl-terminated prepolymers having elevated viscosities, while polyethers having molecular weights of less than 200 form prepolymers having reduced water solubility.

The vinyl compound having a functional group reactive toward isocyanates may, as described above, be a vinyl compound having hydroxyl or amino groups. Preferably, the at least one vinyl compound is accordingly selected from alcohols and amines. Suitable alcohols are, for example, esters of α,β-unsaturated carboxylic acids with a diol, for example 2-hydroxyethyl (meth)acrylate (HEMA), 3- and 2-hydroxypropyl (meth)acrylate (HPMA), 1,3-dihydroxyprop-2-yl (meth)acrylate, 2,3-dihydroxyprop-1-yl (meth)acrylate, 2-, 3- or 4-hydroxybutyl (meth)acrylate and isomers of hydroxyhexyl (meth)acrylates. Also suitable are monoesters of α,β-unsaturated carboxylic acids, for example in the form of (meth)acrylic acid, with polyethylene glycol or polypropylene glycol, 2-hydroxy-3-phenoxypropyl acrylate, adducts of α,β-unsaturated carboxylic acids with caprolactone, amides of α,β-unsaturated carboxylic acids with amino alcohols, such as N-hydroxymethylacrylamide or N-hydroxyethylacrylamide, and addition products thereof with ethylene oxide or propylene oxide, alkanol vinyl ethers, for example 2-hydroxyethyl vinyl ether, 4-vinylbenzyl alcohol or allyl alcohol, and addition products of allyl alcohol and ethylene oxide or propylene oxide, p-methylolstyrene or the like. Preferably, the hydroxy-functional vinyl monomer is selected from the class of the hydroxyalkyl (meth)acrylates. Particularly preferred alcohols are 2-hydroxyethyl methacrylate, 3- and 2-hydroxypropyl (meth)acrylate and allyl alcohol. The expression "2-hydroxypropyl (meth)acrylate" encompasses both possible constitutional isomers, and mixtures thereof.

Suitable amines are primary amines based on amides of (meth)acrylic acid with aliphatic diamines such as ethylenediamine, propylene-1,3-diamine and analogous α,ω-diamines having 4 to 10 carbon atoms and allylamine. Suitable secondary amines are esters of (meth)acrylic acid with amino alcohols such as 2-(tert-butylamino)ethyl (meth)acrylate, and amides of (meth)acrylic acid with amines containing one primary and one secondary amino group, e.g. alkylaminoalkyl (meth)acrylates.

The prepolymer, aside from the aforementioned amine and alcohol constituents, preferably does not contain any significant proportions of further alcohol constituents which are incorporated into the prepolymer via the isocyanate reaction. Thus, the prepolymer appropriately contains, for example, less than 10% by weight, especially less than 5% by weight and more preferably less than 1% by weight of reaction products formed from polyoxyalkylenepolyols based on starter molecules having three or more hydroxyl functionalities, in which all or some of the hydroxyl functionalities have been reacted with methacrylic acid. It is more preferable when the prepolymer consists essentially of the aforementioned alcohol and/or amine constituents and the polyisocyanates mentioned hereinafter (i.e. to an extent of at least 95% by weight and preferably at least 98% by weight); most preferably, the prepolymer consists of these constituents.

The at least one polyisocyanate preferably comprises an aliphatic triisocyanate which can also be formed by trimerization of an aliphatic diisocyanate. In trimers of this kind, the diisocyanate units may be joined by a cyanuric acid function, in each case incorporating one of the isocyanate functions of the diisocyanate. Particularly suitable starting materials for trimers of this kind are, for example, alkylene diisocyanates. More preferably, the polyisocyanate comprises a hexamethylene diisocyanate trimer.

In the context of the present invention, it has also been found to be appropriate when a diisocyanate is additionally incorporated into the prepolymer of the invention as well as a triisocyanate. This diisocyanate is preferably an aliphatic diisocyanate and more preferably isophorone diisocyanate.

The addition of such a diisocyanate in small amounts suppresses solidification (self-thixotropization) of the prepolymer when left to stand for prolonged periods, such that the prepolymer prepared can still be processed without any problem even after prolonged storage.

As stated above, the polyisocyanate has a mean isocyanate functionality in the range from 2.4 to 3.5. Preferred ranges that may be stated for the mean isocyanate functionality are a range from 2.5 to 3.1 and especially from 2.7 to 3.0.

The molar ratio of the polyether i) to the vinyl compound iii) (or the totality of the vinyl compounds) is preferably in the range from 2:1 to 1:2, the result of which is that, given a mean isocyanate functionality of three, an average of at least 1 vinyl compound and at least one polyether radical are present in the prepolymer. A higher proportion of polyether in a polymerization achieves lower crosslinking with a higher proportion of polyethers in the product, which results in better swellability of the product on contact with water. For applications requiring higher swellability, it is therefore possible to set a higher proportion of polyethers in the prepolymer. A higher proportion of vinyl compound iii), by contrast, leads to higher crosslinking and, as a result, to improved mechanical properties. In one embodiment, the molar ratio of the polyether i) to the vinyl compound iii) is in the range from 1:1 to 1:2 and preferably in the range from 1:1.5 to 1:2. In an alternative embodiment, the molar ratio of the polyether i) to the vinyl compound iii) is in the range from 2:1 to 1:1 and preferably in the range from 1.5:1 to 2:1.

The ratio of the sum total of the molar amounts of polyether and vinyl compound to the molar amount of isocyanate groups, as stated above, is in the range from 1.5:1 to 1:1.5. The molar amount of isocyanate groups refers here to the molar amount of isocyanate groups in the mixture, and should not be confused with the molar amount of polyisocyanate. A preferred range that may be specified is that from 1.2:1 to 1:1.2 and especially 1.1:1 to 1:1.1, preference being given to a slight excess of isocyanate, such as a ratio of 1:1.03 to 1:1.1, in order to scavenge any water present in the starting materials.

In general, the proportion of the polyether in the vinyl-terminated prepolymer should be high enough to assure the water solubility of the prepolymer and favorable swellability. A suitable minimum proportion of the polyether that may be specified here is a proportion of at least 30% by weight, based on the total weight of the prepolymer, especially at least 33% by weight, preferably at least 35% by weight and most preferably at least 40% by weight. On the other hand, the proportion of the polyether, based on the total weight of the prepolymer, should not exceed a value of 80% by weight, and values of up to 70% by weight and especially up to 60% by weight may be specified as preferred.

In addition, it is possible, for the reaction by which the vinyl-terminated prepolymer is obtained, to incorporate an aromatic or aliphatic compound having a functional group reactive toward isocyanates, but cannot be qualified either as a polyether or as a vinyl compound iii). For example, by addition of amines or of alcohols, such as ethanol or propanol, it is possible to convert any excess isocyanate functionalities still present after the reaction to urethanes, in order thus to obtain a completely isocyanate-free product. If the prepolymer of the invention is prepared with incorporation of the above-described compounds, the calculation of the sum total of the molar amounts of polyether and vinyl compound should also include the molar amount of these compounds.

The molar amount of the additional aromatic or aliphatic compounds should be no higher than the mean isocyanate functionality of the polyisocyanate minus 2. This ensures that the prepolymer obtained contains an average of one vinyl function and one polyether radical.

A further aspect of the present invention is concerned with processes for preparing the above-described vinyl-terminated prepolymers. Such a process can either be conducted sequentially, by first reacting one of the components having a functional group reactive toward isocyanates (i.e. the polyether or the vinyl compound) with the at least one polyisocyanate to obtain an intermediate, and then adding the second component having a functional group reactive toward isocyanates, such that this component can react with the isocyanate functions that remain in the intermediate. However, it is also possible to convert all constituents i) to iii) in a one-pot reaction, which is preferable because of the easier process procedure and the small amount of time required to obtain the end product.

In one embodiment, said process for preparing a vinyl-terminated prepolymer as described above is a process comprising
  i) the addition of at least one polyisocyanate having a mean isocyanate functionality in the range from 2.4 to 3.5 either to a polyether having a functional group reactive toward isocyanates or to at least one vinyl compound having a functional group reactive toward isocyanates,
  ii) allowing the isocyanate groups to react with the functional groups reactive toward isocyanates,
  iii) depending on the constituent initially charged in step i), the addition of the other constituent to the reaction product formed from polyisocyanate and the initially charged constituent, and
  iv) allowing the reaction product formed from polyisocyanate and the initially charged constituent to react with the other constituent.

Said "other constituent" is the at least one vinyl compound having a functional group reactive toward isocyanates when the constituent initially charged in step i) is the polyether having a functional group reactive toward isocyanates, and vice versa.

In a further embodiment, said process for preparing a vinyl-terminated prepolymer as described above is a process comprising
  i) the addition of at least one polyisocyanate having a mean isocyanate functionality in the range from 2.4 to 3.5 to a mixture of a polyether having a functional group reactive toward isocyanates and at least one vinyl compound having a functional group reactive toward isocyanates, and
  ii) allowing the polyisocyanate to react with the polyether and the vinyl compound.

The aforementioned processes can be optimized in relation to the achievable reaction rate by the addition of a catalyst that accelerates the reaction of the isocyanate groups with the functional groups reactive toward isocyanates. Suitable catalysts in this context are all known catalysts for the formation of urethanes, such as tertiary amines, and metal salts, such as tin salts, titanium salts and bismuth salts. Particularly suitable catalysts are dibutyltin laurate and bismuth neodecanoate.

With regard to the proportion of the catalyst to be incorporated, the present invention is not subject to any relevant restrictions, with the proviso that the proportion of the catalyst should be restricted to a minimum required. Particularly suitable proportions of catalyst are in the range from 0.001% to 1 by weight and preferably 0.005% to 0.1% by weight.

It may additionally be advisable to add a free-radical stabilizer to the reaction mixture, in order to prevent premature polymerization of the vinyl-terminated prepolymer obtained. Suitable stabilizers are, for example, OH-TEMPO (4-hydroxy-2,2,6,6-tetramethylpiperidin-1-oxyl) or hydroquinone monomethyl ether.

A further aspect of the present invention relates to the use of a vinyl-terminated prepolymer as described above as an injection medium or constituent of an injection medium for rock or soil consolidation. In addition, it is possible to use injection media of this kind, for example, for sealing of built structures, tunnels or mines. In the context of this use, the vinyl-terminated prepolymer is injected into a cavity together with a free-radical initiator and optionally further components and appropriately polymerized therein.

As well as the vinyl-terminated prepolymers described, the injection medium may comprise further vinyl monomers such as (meth)acrylates in particular. Free-radical initiators used for the polymerization mentioned may be known initiators for free-radical reactions, for example alkali metal persulfates, ammonium persulfates and hydrogen peroxides or azobisisobutyronitrile (AIBN) or organic peroxides such as dibenzoyl peroxide. When the injection medium contains water as an additional component, preference is given to the use of a water-soluble catalyst in the form of an alkali metal persulfate or ammonium persulfate.

The free-radical initiator is typically used in an amount of 0.01% to 5% by weight, especially 0.05% to 3% by weight, preferably 0.5% to 1.5% by weight, based on the overall composition.

In addition to the free-radical initiator, it is possible to use a co-initiator which is often also referred to as accelerator. This co-initiator is especially a tertiary amine, a transition metal salt or a transition metal complex. Tertiary amines suitable as co-initiator are especially selected from the group consisting of di- or trialkanolamines, preferably di- or triethanolamine or a mixture thereof, N,N-dimethylaniline, N,N-diethylaniline, N,N-bis(hydroxyalkyl)anilines such as N,N-bis(2-hydroxyethyl)aniline, N,N-alkylhydroxyalkylanilines such as N-ethyl-N-hydroxyethylaniline, N,N-dimethyl-p-toluidine, N,N-diethyl-p-toluidine, N-methyl-N-hydroxyethyl-p-toluidine, N,N-bis(2-hydroxyethyl)-p-toluidine and alkoxylated N,N-bis(hydroxyethyl)-p-toluidines, N-ethoxylated p-toluidine, N,N-bis(2-hydroxyethyl)xylidine, N-alkylmorpholine and mixtures thereof. Suitable transition metal salts and transition metal complexes are, for example, salts and complexes of cobalt, nickel, copper, manganese or vanadium.

The injection medium may additionally comprise liquid additives, for example in the form of aqueous polymer dispersions or polyethylene glycols. In the present document, aqueous polymer dispersions are understood to mean polymer dispersions wherein the solid polymer constituents are either already dispersed in water prior to the production of the injection medium or are solid, especially pulverulent, polymer dispersion components which only come into contact with water and are dispersible therein when the injection medium is used. According to the embodiment of the injection medium, the aqueous polymer dispersion is used in the form of a dispersible solid or of an already dispersed solid. Particularly suitable aqueous polymer dispersions, in the context of the present invention, are those based on (meth)acrylate polymers, copolymers of (meth)acrylates and styrene, copolymers of styrene and butadiene, and copolymers of vinyl acetate, ethylene and optionally a vinyl ester.

Additionally or alternatively, it is possible to add an ultrafine cement to the injection medium, having a fineness (determined from the sieve residue) of not more than $d_{95} \leq 16$ μm, preferably $d_{95} \leq 10$ μm and most preferably of $d_{95} \leq 6$ μm.

In addition, the injection medium may comprise dyes. It is preferable when the injection medium does not comprise any viscosity-increasing constituents since this can impair the function of the injection medium. It is particularly preferable when the injection medium consists of the aforementioned constituents, i.e. the prepolymer, optionally water, free-radical initiator, co-initiator, and optionally aqueous polymer dispersions or polyethylene glycols and/or ultrafine cement. A further aspect of the present invention relates to an injection medium comprising or consisting of a vinyl-terminated prepolymer as described above for sealing of built structures, tunnels or mines, for example, wherein the injection medium comprises, as further constituents, a catalyst and optionally the additives described above for the corresponding use.

A further aspect of the present invention relates to the use of a vinyl-terminated prepolymer as described above for production of superabsorbents, wherein the prepolymer is polymerized, optionally with further vinyl monomers. Suitable further vinyl monomers are especially (meth)acrylates, preferably (meth)acrylates that are ionic and especially anionic at neutral pH (i.e. pH 7), and more preferably acrylic acid or methacrylic acid (these are in deprotonated form at neutral pH).

A further aspect of the present invention relates to superabsorbents obtainable by polymerizing a vinyl-terminated prepolymer as described above, optionally with addition of further vinyl monomers, according to the above specifications.

Finally, a further aspect of the present invention relates to the use of a vinyl-terminated prepolymer as described above for production of concrete plasticizers, wherein the prepolymer is polymerized, optionally with further monomers. In this case too, the further monomers to be incorporated are appropriately polar, preferably ionic and especially anionic monomers which more preferably comprise acrylic acid or methacrylic acid.

Finally, a last aspect of the present invention relates to a concrete plasticizer obtainable by homopolymerization of a vinyl-terminated prepolymer as described above or by copolymerization of these vinyl-terminated prepolymers with other vinyl monomers. In the context of this aspect, the prepolymers should have an average of only one vinyl function. A higher proportion of vinyl functions can result in crosslinking of the polymers formed, which has an adverse effect on the properties of the polymer as a concrete plasticizer. The vinyl monomers to be incorporated for the production of the concrete plasticizer correspond to the vinyl monomers mentioned above for the use of the vinyl-terminated prepolymer for production of concrete plasticizers.

The prepolymers of the invention have the advantage over the prepolymers based on polyethers that are known from the prior art of a low viscosity with simultaneously high water solubility. If these prepolymers are employed for production of injection media, it is possible to control the mechanical strength, ultimate elongation, swelling characteristics and water solubility via the ratio of vinyl compound to polyether. In addition, the prepolymers of the invention contain only few ester bonds in relation to their molecular weight, which results in improved stability with respect to alkaline media.

The present invention is to be illustrated in detail hereinafter with reference to a few examples, but this is not to be associated with any restriction of the concept of the invention.

EXAMPLES

Determination of the Relevant Properties

The viscosities of the prepolymers and of the 50% aqueous solutions of the prepolymers were determined at 23° C. with a Physica MCR101 viscometer according to ISO 3219 with a coaxial cylinder measurement system (at a cone angle of 120°).

The appearance of the 50% aqueous solution was determined by inspection. The observation "clear" indicates that the polymer had dissolved.

The gel time was determined for a 50% aqueous solution of the prepolymers (25 g) with addition of 0.5 g of a 10% solution of sodium persulfate in water and 0.25 g of triethanolamine. The gel time corresponds to the time before which the first gel structures are visually apparent in the reaction solution.

Materials Used:

| | |
|---|---|
| Aduxol VP-6685 | polyethylene oxide/polypropylene oxide block copolymer with a molecular weight Mw of 2258 and an ethylene oxide content of 41%; the ethylene oxide forms the end blocks (Schärer & Schläpfer AG) |
| Aduxol VP-11115 | polyethylene oxide/polypropylene oxide block copolymer with a molecular weight Mw of 1700 and an ethylene oxide content of 50%; the ethylene oxide forms the middle block (Schärer & Schläpfer AG) |
| Aduxol VP-11122 | mono-methoxy-terminated polyethylene oxide/polypropylene oxide block copolymer with a molecular weight Mw of 500 and an ethylene oxide content of 50%; the polyethylene oxide is methoxy-modified (Schärer & Schläpfer AG) |
| Aduxol VP-11121 | mono-methoxy-terminated polyethylene oxide/polypropylene oxide block copolymer with a molecular weight Mw of 1000 and an ethylene oxide content of 50%; the polyethylene oxide is methoxy-modified (Schärer & Schläpfer AG) |
| Aduxol VP-11132 | mono-methoxy-terminated polyethylene oxide/polypropylene oxide block copolymer with a molecular weight Mw of 500 and an ethylene oxide content of 50%; the polypropylene oxide is methoxy-modified (Schärer & Schläpfer AG) |
| Aduxol VP-11128 | mono-methoxy-terminated polyethylene oxide/polypropylene oxide block copolymer with a molecular weight Mw of 1000 and an ethylene oxide content of 50%; the polypropylene oxide is methoxy-modified (Schärer & Schläpfer AG) |
| MPEG500 | mono-methoxy-terminated polyethylene glycol with a molecular weight Mw of 500 (BASF) |
| Desmodur T80P | mixture of tolylene 2,4- and 2,6-diisocyanate in a ratio of 80:20 (Bayer) |
| Vestanat IPDI | isophorone diisocyanate (Evonik) |
| Desmodur N3300 | hexamethylene diisocyanate trimer (Bayer) |
| 2-tBAEMA | 2-(tert-butylamino)ethyl methacrylate (BASF) |
| DBTL | dibutyltin dilaurate, catalyst (Azelis) |
| OH-TEMPO | 4-hydroxy-2,2,6,6-tetramethylpiperidin-1-oxyl, free-radical scavenger (Evonik) |

Preliminary Experiments

In preliminary experiments, first of all, prepolymers based on isocyanates and polyether diols were prepared (V-1 to V-3). For this purpose, the polyether diols were reacted in a first stage with diisocyanates to give an intermediate. In a second stage, hydroxyethyl methacrylate (HEMA) was then added, in order to modify the isocyanate groups still present with vinyl functionalities.

In experiments V-1 and V-3, however, the system was already found to be completely polymerized after the first stage. When an aliphatic isocyanate (V-2) was used in place of an aromatic diisocyanate, a product that had a viscosity of about 50 000 mPas was obtained after the second stage.

In a second set of experiments, a trifunctional isocyanate (Desmodur N3300) was reacted first with hydroxyethyl methacrylate and, in V-4, additionally with MPEG 500. The intermediate obtained was reacted in a second step with a dihydroxy-functional polyether (Aduxol VP-6685) to give the end product. In experiments V-4 to V-6, however, a very high viscosity of about 100 000 mPas or more was found for the products obtained, which indicates a significant proportion of chain extension.

The results of these preliminary studies and the compositions of the products are shown in table 1 below.

TABLE 1

|  | V-1 | V-2 | V-3 | V-4 | V-5 | V-6 |
|---|---|---|---|---|---|---|
| 1st stage |  |  |  |  |  |  |
| Aduxol VP-6685 | 100 | 100 |  |  |  |  |
| Aduxol VP-11115 |  |  | 100 |  |  |  |
| MPEG 500 |  |  |  | 62 |  |  |
| Desmodur T8OP | 17.5 |  | 22.5 |  |  |  |
| Vestanat IPDI |  | 22.1 |  |  |  |  |
| Desmodur N3300 |  |  |  | 59.4 | 57.8 | 122 |
| HEMA |  |  |  | 9.8 | 13 | 55 |
| Ethanol |  |  |  |  | 4.6 |  |
| DBTL |  | 0.005 |  | 0.01 | 0.01 | 0.01 |
| OH-Tempo |  |  |  | 0.02 | 0.02 | 0.02 |
| 2nd stage |  |  |  |  |  |  |
| DBTL | 0.005 |  |  |  |  |  |
| OH-TEMPO | 0.02 | 0.02 | 0.02 |  |  |  |
| HEMA | 13 | 12.9 | 16.7 |  |  |  |
| Aduxol VP-6685 |  |  |  | 94 | 94 | 185 |
| Properties |  |  |  |  |  |  |
| Viscosity of the prepolymer [mPa·s] | reaction mixture polymerizes in 1st stage | 50000 | reaction mixture polymerizes in 1st stage | 99000 | 250000 | 340000 |
| Appearance of the 50% aqueous solution | — | clear | — | clear | clear | clear |
| Viscosity as a 50% aqueous solution [mPa·s] | — | 1200 | — | 3740 | 38000 | 15000 |
| Gel time [min] | — | 40 | — | 29 | 12 | 7 |

Example 1

Inventive compositions 1 to 8 were prepared by reacting, in a one-pot reaction (compositions 1 to 7) or in a two-stage reaction, various polyethers functionalized with methoxy groups at one end and having a hydroxyl function with a trifunctional isocyanate (Desmodur N3300) and a hydroxy-functional acrylate (hydroxyethyl methacrylate or hydroxypropyl methacrylate (HPMA); compositions 1 to 7) or an amine-functional acrylate ((2-(tert-butylamino)ethyl methacrylate; composition 8). All products exhibited viscosities in the range from about 10 000 to 50 000 mPa·s and had good processability. The gel time of the compositions obtained was in the range from 7 to 30 min. The exact compositions and the particular properties thereof are shown in table 2.

TABLE 2

|  | 1 | 2 | 3 | 4 | 5 | 6 | 7 | 8 |
|---|---|---|---|---|---|---|---|---|
| 1st stage |  |  |  |  |  |  |  |  |
| Aduxol VP-11122 | 75 |  |  |  |  |  |  |  |
| Aduxol VP-11121 |  | 143 |  |  |  |  |  |  |
| Aduxol VP-11132 |  |  | 75 |  |  |  |  |  |
| Aduxol VP-11128 |  |  |  | 143 |  |  |  |  |
| MPEG500 |  |  |  |  | 60 | 75 | 75 | 75 |

TABLE 2-continued

|  | 1 | 2 | 3 | 4 | 5 | 6 | 7 | 8 |
|---|---|---|---|---|---|---|---|---|
| Desmodur N3300 | 61 | 61 | 61 | 61 | 61 | 61 | 61 | 61 |
| HEMA | 20.6 | 20.6 | 20.6 | 20.6 | 24.7 | 20.6 | | |
| HPMA | | | | | | | 22.8 | |
| DBTL | 0.01 | 0.01 | 0.01 | 0.01 | 0.01 | 0.01 | 0.01 | 0.01 |
| OH-Tempo | 0.02 | 0.02 | 0.02 | 0.02 | 0.02 | 0.02 | 0.02 | 0.02 |
| 2nd stage | | | | | | | | |
| 2-tBAEMA | | | | | | | | 29.3 |
| Properties | | | | | | | | |
| Viscosity of the prepolymer [mPa · s] | 18000 | 25000 | 50000 | 40000 | 23000 | 9250 | 9550 | 13600 |
| Appearance of the 50% aqueous solution | clear | clear | clear | clear | clear | clear | clear | clear |
| Viscosity as a 50% aqueous solution [mPa · s] | 4980 | 13500 | 2035 | 1720 | 9100 | 2175 | 2450 | 6700 |
| Gel time | 7 | 10 | 11 | 30 | 30 | 24 | 22 | 10 |

Example 2

In further studies, the effect of an addition of difunctional isocyanates on the prepolymers obtained was to be examined. The reference example used for these studies was composition 5 containing trifunctional isocyanate only. In compositions 9, 10 and 11, the mean NCO functionality was reduced to 2.75 or 2.5. In comparative composition 7, the mean NCO functionality was reduced further to 2.24. However, this composition was found to polymerize completely, and so the product obtained had no further utility. Compositions 9 to 11 were still liquid even after storage at room temperature for 2 months, while the prepolymer according to composition 5 solidified after only 2 weeks. In addition, it was not possible to observe any air (in the form of bubbles) in the solution in the case of the 50% solutions of compositions 9 to 11, which was the case for reference composition 5.

The exact compositions of the samples studied and the particular properties thereof are shown in table 3 below.

In a further series of experiments, the effect of different ratios of MPEG 500 and HEMA on the polymer formed was examined. Example 6 was used as a reference for these studies, in which the ratio of MPEG 500 to HEMA was 1:1. In examples 12 and 13, this ratio was adjusted to 1:2 and 2:1 respectively. It was found here that the change in the ratio had only a slight effect on the properties of the prepolymer formed. In all cases, products of good processability were obtained.

TABLE 3

|  | 5 | 9 | 10 | 11 | V-7 | 6 | 12 | 13 |
|---|---|---|---|---|---|---|---|---|
| 1st stage | | | | | | | | |
| MPEG500 | 60 | 60 | 60 | 50 | 60 | 75 | 100 | 100 |
| Desmodur N3300 | 61 | 45.8 | 30.5 | 45.8 | 15.3 | 61 | 122 | 61 |
| IPDI | | 8.8 | 17.6 | 8.8 | 26.4 | | | |
| HEMA | 24.7 | 24.7 | 24.7 | 27.5 | 24.7 | 20.6 | 55 | 13.7 |
| DBTL | 0.01 | 0.01 | 0.01 | 0.01 | 0.01 | 0.01 | 0.01 | 0.01 |
| OH-Tempo | 0.02 | 0.02 | 0.02 | 0.02 | 0.02 | 0.02 | 0.02 | 0.02 |
| Ø NCO functionality | 3 | 2.75 | 2.5 | 2.75 | 2.24 | 3 | 3 | 3 |
| Properties | | | | | | | | |
| Viscosity of the prepolymer [mPa · s] | 23000 | 18000 | 14000 | 14000 | polymerizes | 9250 | 31000 | 7600 |
| Appearance of the 50% aqueous solution | clear | clear | milky | opaque | — | clear | clear | clear |
| Viscosity as a 50% aqueous solution [mPa · s] | 9100 | 1400 | 1000 | 1350 | — | 2175 | n.d. | 3450 |
| Gel time [min] | 30 | 20 | 25 | 12 | — | 24 | 15 | 22 | n.d. = not determined.

Example 3

In the context of this example, the extent to which the preparation of the vinyl-terminated prepolymers within a sequential or one-pot process affects the resultant properties of the prepolymers was to be examined. For this purpose, in composition 14, MPEG 500 was first reacted with a trifunctional isocyanate (Desmodur N3300) and the product obtained was reacted with hydroxyethyl methacrylate in a second stage to give the end product. In composition 15, the trifunctional isocyanate was first reacted with hydroxyethyl methacrylate and the product obtained was then reacted with MPEG 500 to give the end product. In composition 12, all the components were reacted with one another in a one-pot process. It was found here that the exact process procedure had only a minor effect on the viscosity of the prepolymer obtained (see table 4). Since the one-pot process is associated with the lowest time demands, this process is preferred for the production of the vinyl-terminated prepolymers of the invention.

TABLE 4

|  | 12 | 14 | 15 |
|---|---|---|---|
| 1st stage | | | |
| MPEG500 | 100 | 100 | |
| Desmodur N3300 | 122 | 122 | 122 |
| HEMA | 55 | | 55 |
| DBTL | 0.01 | 0.01 | 0.01 |
| OH-Tempo | 0.02 | 0.02 | 0.02 |
| 2nd stage | | | |
| HEMA | | 55 | |
| MPEG500 | | | 100 |
| Properties | | | |
| Viscosity of the prepolymer [mPa · s] | 31000 | 30000 | 14000 |

The invention claimed is:

1. A method for sealing of built structures, tunnels or mines with an injection medium, comprising:
providing an injection medium comprising a vinyl-terminated prepolymer by reaction of
 i) a polyether having a functional group reactive toward isocyanates with
 ii) at least one polyisocyanate having a mean isocyanate functionality in the range from 2.4 to 3.5, and
 iii) at least one vinyl compound having a functional group reactive toward isocyanates,
 wherein the molar ratio of polyether i) to vinyl compound iii) is in the range from 3:1 to 1:3 and the ratio of the sum total of the molar amounts of polyether and vinyl compound to isocyanate groups ii) is in the range from 1.5:1 to 1:1.5,
 wherein the polyether has exactly one functional group reactive with NCO group or the vinyl compound has exactly one functional group reactive with NCO group,
 wherein the proportion of the polyether in the vinyl-terminated prepolymer obtained via the reaction amounts to at least 30% by weight, based on the total weight of the prepolymer, and
 wherein the vinyl-terminated prepolymer is injected into a cavity together with a free-radical initiator and optionally further components; and
polymerizing said injection medium.

2. The method as claimed in claim 1, wherein the prepolymer contains less than 10% by weight of reaction products formed from polyoxyalkylenepolyols based on starter molecules having three or more hydroxyl functionalities, in which all or some of the hydroxyl functionalities have been reacted with methacrylic acid.

3. The method as claimed in claim 1, wherein the polyether having a functional group reactive toward isocyanates is a linear polyethylene glycol, polypropylene glycol or a mixed polyethylene glycol/polypropylene glycol copolymer or block copolymer.

4. The method as claimed in claim 1, wherein the polyether having a functional group reactive toward isocyanates has a molecular weight Mw in the range from 200 to 5000.

5. The method as claimed in claim 1, wherein the at least one vinyl compound is selected from alcohols, hydroxyethyl (meth)acrylate and hydroxypropyl (meth)acrylate, and amines.

6. The method as claimed in claim 1, wherein the at least one polyisocyanate comprises a triisocyanate.

7. The method as claimed in claim 6, wherein the at least one polyisocyanate additionally comprises an aliphatic diisocyanate.

8. The method as claimed in claim 1, wherein the reaction additionally includes iv) an aromatic or aliphatic compound which cannot be qualified either as a polyether i) or as a vinyl compound iii), having a functional group reactive toward isocyanates.

9. A process for producing an injection medium, comprising preparing a vinyl-terminated polymer by a method comprising:
 i) the addition of at least one polyisocyanate having a mean isocyanate functionality in the range from 2.4 to 3.5 either to a polyether constituent having a functional group reactive toward isocyanates or to at least one vinyl compound constituent having a functional group reactive toward isocyanates,
 ii) allowing the isocyanate groups to react with the functional groups reactive toward isocyanates,
 iii) depending on the constituent initially charged in step i), the addition of the other constituent to the reaction product formed from polyisocyanate and the initially charged constituent, and
 iv) allowing the reaction product formed from polyisocyanate and the initially charged constituent to react with the other constituent,
 wherein the other constituent is the at least one vinyl compound constituent having a functional group reactive toward isocyanates when the constituent initially charged in step i) is the polyether constituent having a functional group reactive toward isocyanates, and vice versa, and the addition of a free-radical initiator and optionally further components,
 wherein the molar ratio of polyether to vinyl compound is in the range from 3:1 to 1:3 and the ratio of the sum total of the molar amounts of polyether and vinyl compound to isocyanate groups ii) is in the range from 1.5:1 to 1:1.5,
 wherein the polyether has exactly one functional group reactive with NCO group or the vinyl compound has exactly one functional group reactive with NCO group,
 wherein the proportion of the polyether in the vinyl-terminated prepolymer obtained via the reaction amounts to at least 30% by weight, based on the total weight of the polymer.

10. A process for producing an injection medium, comprising the preparation of a vinyl-terminated prepolymer by a method comprising:
 i) the addition of at least one polyisocyanate having a mean isocyanate functionality in the range from 2.4 to 3.5 to a mixture of a polyether having a functional group reactive toward isocyanates and at least one vinyl compound having a functional group reactive toward isocyanates,
 ii) allowing the polyisocyanate to react with the polyether and the vinyl compound,
 wherein the molar ratio of polyether to vinyl compound is in the range from 3:1 to 1:3 and the ratio of the sum total of the molar amounts of polyether and vinyl compound to isocyanate groups ii) is in the range from 1.5:1 to 1:1.5, wherein the polyether has exactly one functional group reactive with NCO group or the vinyl compound has exactly one functional group reactive with NCO group, wherein the proportion of the polyether in the vinyl-terminated prepolymer obtained via the reaction amounts to at least 30% by weight, based on the total weight of the polymer.

11. The process as claimed in claim 9, wherein, for the reaction of the isocyanate groups with the functional groups reactive toward isocyanates, a catalyst is added.

12. The method as claimed in claim 1, wherein the proportion of the polyether in the vinyl-terminated prepolymer amounts to at least 33% by weight, based on the total weight of the prepolymer.

13. The method as claimed in claim 2, wherein the prepolymer contains less than 5% by weight of reaction products formed from polyoxyalkylenepolyols based on starter molecules having three or more hydroxyl functionalities, in which all or some of the hydroxyl functionalities have been reacted with methacrylic acid.

14. The method as claimed in claim 3, wherein the polyether having a functional group reactive toward isocyanates is a polyethylene glycol modified at one end with an alkoxy group, preferably a methoxy group.

15. The method as claimed in claim 4, wherein the polyether having a functional group reactive toward isocyanates has a molecular weight Mw in the range from 300 to 2000.

16. The method as claimed in claim 5, wherein the at least one vinyl compound is selected from an allyl alcohol and 2-(tert-butylamino)ethyl methacrylate.

17. The method as claimed in claim 6, wherein the at least one polyisocyanate comprises an aliphatic triisocyanate.

18. The method as claimed in claim 6, wherein the at least one polyisocyanate comprises a trimer of hexamethylene diisocyanate.

19. The method as claimed in claim 7, wherein the at least one polyisocyanate additionally comprises an isophorone diisocyanate.

20. The method as claimed in claim 1, wherein the polyether has exactly one functional group reactive with NCO group and the vinyl compound has exactly one functional group reactive with NCO group.

* * * * *